(12) United States Patent
Fanton et al.

(10) Patent No.: US 6,744,850 B2
(45) Date of Patent: Jun. 1, 2004

(54) X-RAY REFLECTANCE MEASUREMENT SYSTEM WITH ADJUSTABLE RESOLUTION

(75) Inventors: Jeffrey T. Fanton, Los Altos, CA (US); Craig Uhrich, Redwood City, CA (US); Louis N. Koppel, San Jose, CA (US)

(73) Assignee: Therma-Wave, Inc., Fremont, CA (US)

( * ) Notice: Subject to any disclaimer, the term of this patent is extended or adjusted under 35 U.S.C. 154(b) by 141 days.

(21) Appl. No.: 10/053,373

(22) Filed: Oct. 24, 2001

(65) Prior Publication Data

US 2002/0097837 A1 Jul. 25, 2002

Related U.S. Application Data

(60) Provisional application No. 60/261,154, filed on Jan. 11, 2001.

(51) Int. Cl.[7] .................................................. G01T 1/36
(52) U.S. Cl. .............................. 378/83; 378/82; 378/70
(58) Field of Search .............................. 378/83, 82, 84, 378/88, 89, 70, 45, 55, 90, 71, 81

(56) References Cited

U.S. PATENT DOCUMENTS

| | | | | |
|---|---|---|---|---|
| 4,169,228 A | * | 9/1979 | Briska et al. | 378/45 |
| 4,260,898 A | * | 4/1981 | Annis | 378/146 |
| 4,649,559 A | * | 3/1987 | Wang | 378/146 |
| 5,042,951 A | | 8/1991 | Gold et al. | 356/369 |
| 5,268,953 A | * | 12/1993 | Van Vlijmen | 378/79 |
| 5,412,473 A | | 5/1995 | Rosencwaig et al. | 356/351 |
| 5,619,548 A | | 4/1997 | Koppel | 378/70 |
| 6,069,934 A | * | 5/2000 | Verman et al. | 378/73 |
| 6,381,303 B1 | * | 4/2002 | Vu et al. | 378/64 |

FOREIGN PATENT DOCUMENTS

| WO | WO 92/08104 | 5/1992 | G01B/11/24 |
|---|---|---|---|
| WO | WO 00/57127 | 9/2000 | G01B/11/06 |
| WO | WO 01/71325 | 9/2001 | G01N/23/00 |

OTHER PUBLICATIONS

K. Sakurai et al., "Fourier Analysis of Interference Structure in X-Ray Specular Reflection from Thin Films," *Jpn. J. Appl. Phys.*, vol. 31. Part 2, No. 2A, Feb. 1, 1992, pp. L113–L115.
K.N. Stoev et al., "Review on grazing incidence X-ray spectrometry and reflectometry," *Spectrochimica Acta Part B*, vol. 54, 1999, pp. 41–82.
N. Wainfan et al., "Density Measurements of Some Thin Copper Films," *Journal of Applied Physics*, vol. 30, No. 10, Oct. 1959, pp. 1604–1609.
J.P. Sauro et al., "Some Observations on the Interference Fringes Formed by X Rays Scattered from Thin Films," *Physical Review*, vol. 143, No. 1, Mar. 1966, pp. 439–443.
K. Sakurai et al., "Analysis of thin films by X-ray scattering at grazing incidence," *Spring–8 User Experiment Report No. 2 (1998 A)*, Mar. 1999, p. 162.
J.M. Grimal et al., "X-ray reflectivity: a new tool for the study of glass surfaces," *Journal of Non–Crystalline Solids*, vol. 196, 1996, pp. 128–133.

(List continued on next page.)

*Primary Examiner*—Craig E. Church
*Assistant Examiner*—Irakli Kiknnadze
(74) *Attorney, Agent, or Firm*—Stallman & Pollock LLP

(57) ABSTRACT

An x-ray reflectometry system for measuring thin film samples. The system includes an adjustable x-ray source, such that characteristics of an x-ray probe beam output by the x-ray source can be adjusted to improve the resolution of the measurement system. The x-ray probe beam can also be modified to increase the speed of evaluating the thin film sample, for situations where some degree of resolution can be sacrificed. In addition, or alternatively, the system can also provide an adjustable detector position device which allows the position of the detector to be adjusted to increase the resolution of the system, or to reduce the time it takes to evaluate the thin film material.

33 Claims, 6 Drawing Sheets

OTHER PUBLICATIONS

P. Polouček et al., "X-ray reflectivity analysis of thin complex Langmuir-Blodgett films," *Journal of Physics D: Applied Physics*, vol. 34, 2001, pp. 450-458.

C.E. Bouldin et al., "Thermal expansion coefficients of low-k dielectric films from Fourier analysis of x-ray reflectivity," *Journal of Applied Physics*, vol. 88, No. 2, Jul. 15, 2000, pp. 691-695.

Wen-Li Wu et al., "Study of ultra-thin hydrogen silsesquioxane films using X-ray reflectivity," *Thin Solid Films*, vol. 312, 1998, pp. 73-77.

E.K. Lin et al., "Structure and Property Characterization of Porous Low-k Dielectric Constant Thin Films using X-ray Reflectivity and Small Angle Neutron Scattering," *Mat. Res. Soc. Symp. Proc.*, vol. 612, 2000 [Materials Research Society], pp. D4.1.1-D4.1.8.

B.J. Bauer et al., "Structure and Property Characterization of Low-k Dielectric Porous Thin Films," Electronics Materials 30(4), pp. 304-308, 2001.

P. Boher et al., "Radio frequency sputtering of tungsten/tungsten nitride multilayers of GaAs," *J. Vac. Sci. Technol. A*, vol. 8, No. 2, Mar./Apr. 1990, pp. 846-849.

E. Chason et al., "In situ energy dispersive x-ray reflectivity measurements of H ion bombardment on $SiO_2/Si$ and Si," *Appl. Phys. Lett.*, vol. 60, No. 19, May 11, 1992, pp. 2353-2355.

N. Awaji et al., "High-Accuracy X-ray Reflectivity Study of Native Oxide Formed in Chemical Treatment," *Jpn. J. Appl. Phys.*, vol. 34, 1995, pp. L1013-L1016.

W.C. Johnson et al., "Rapid X-Ray reflectometry (XRR) metrology applied to Cu/low-k Damascene process development," In *Process Control and Diagnostics, Proceedings of SPIE*, vol. 4182, 2000, pp. 106-114.

B. Poumellec et al., "A new method to extract the X-ray absorption fine structures from the reflectivity spectra: application to the study of $(Ti.Nb)O_2$ amorphous solid solutions," *Physica B*, vol. 158, 1989, pp. 282-283..

* cited by examiner

X-RAY REFLECTANCE MEASUREMENT SYSTEM WITH ADJUSTABLE RESOLUTION

RELATED APPLICATION

The present application claims the benefit of U.S. Provisional Application Serial No. 60/261,154, filed Jan. 11, 2001, titled X-RAY REFLECTANCE MEASUREMENT SYSTEM WITH ADJUSTABLE RESOLUTION.

TECHNICAL FIELD

X-ray reflectometry (XRR) is a technique for measuring the thickness of thin films in semiconductor manufacturing and other applications. The present invention relates to such a measurement system and provides for making adjustments to components of the system to improve the operation of the system.

BACKGROUND OF THE INVENTION

There has been significant interest in developing x-ray reflectance techniques for analyzing thin films, and particularly thin metal films. Thin metal films are not easily analyzed using conventional optical metrology techniques that rely on visible or UV wavelengths since metal films are opaque at those wavelengths. X-rays are of interest since they can penetrate metals.

The basic concepts behind measuring thin metal films on a substrate using an x-ray reflectance technique are described in U.S. Pat. No. 5,619,548, issued Apr. 8, 1997, and incorporated herein by reference. As described therein, a beam of x-rays is focused to strike the thin metal sample over a range of angles from near grazing incidence to a few degrees. A photodetector array detects the reflected x-rays over a range of angles of incidence. In this configuration, interference effects are created between the x-rays which reflect off the upper surface of the sample and at the interface between the thin film layer and the substrate. These interference effects vary as a function of angle of incidence. A plot of the change in intensity of the x-rays detected at the photodetector as a function of angle of incidence reveals periodic fringes, the spacing of which is a function of film thickness. Additional film properties, such as density and surface roughness, can be inferred from other characteristics of the reflectivity profile, such as the fringe amplitude or the location of the critical angle (onset of total external reflection).

As with many systems, there are many trade-offs involved in the design parameters of an XRR system. For example, as the thickness of the films being measured increases, the spacing (as a function of angle of incidence) between the fringes becomes smaller. In order to be able to analyze such closely spaced fringes, it is desirable to maximize the resolution of the system. In particular, the spread of angles of incidence detected by any one pixel in the detector array should be as small as possible.

One drawback associated with increasing the resolution of the system is that the flux or amount of energy received by each pixel is typically reduced. Reduced flux results in a less favorable signal to noise performance which in turn increases the time needed for successful measurements. While the trade-off may be required to measure thicker films, this increase in time would be an undesirable, and unnecessary, penalty when measuring thinner films.

Typically systems are designed to balance the need to make measurements of thicker films which require higher resolution, with the need to make measurements of thinner films quickly and efficiently. The goal is to balance these competing factors so that the resulting measurement instrument will have a good balance between resolution and signal to noise performance. However, such systems do not allow physical characteristics of the measurement instrument to be adjusted to optimize them for measuring different films with a range of different thickness.

It was recognized by the inventors herein that an improved system would allow the operator the freedom to adjust the resolution to best suit the measurement of a particular sample. For example, when measuring very thin films, the fringe spacing is quite large and high resolution is less important. In such a case, it would be helpful if the user could adjust the system to increase the flux thereby improving signal to noise performance and measurement speed. One design approach for increasing the flux is to move the detector array closer to the sample. Another approach is to tilt the X-Ray source such that apparent width of the source, as imaged on the sample, is increased.

When measuring thicker films, the spacing between fringes is reduced. In such a case, having a high-resolution system is critical in being able to obtain accurate measurements. Therefore, it would be helpful if the operator could maximize resolution even if it meant that measurement time would be increased, since without sufficient resolution, information about the layer could not be derived at all. One design approach for increasing resolution is to move the detector array farther away from the sample. Another approach is to tilt the X-Ray source such that apparent width of the source, as imaged on the sample, is reduced.

SUMMARY

In order to achieve these goals, the inventors herein propose an XRR system that includes one or more mechanisms that would permit the operator to adjust the resolution of the system for a particular measurement. In one embodiment, the operator is able to adjust the distance of the photodetector array from the sample. As this distance is increased, the resolution will be increased.

In another embodiment, the user is able to control the effective width of the x-ray probe beam imaged on the sample. The smaller the effective width of the x-ray probe beam, the higher the resolution. The effective width is controlled by adjusting the angle of the x-ray emission material.

Such a system can be implemented in a simultaneous multiple angle of incidence XRR system of the type described in the above-cited U.S. Patent. Further details of an embodiment of an XRR system developed by the assignee herein can be found in PCT Publication WO 01/71325 A2 published Sep. 27, 2001, and incorporated herein by reference (referred to herein as the '325 application).

DETAILED DESCRIPTION

As discussed above, x-ray reflectometry (XRR) is a technique whereby the reflectivity of a sample is measured at x-ray wavelength (Ångstrom range) over a spread of angles. These angles typically range from 0° (grazing incidence along the surface of the sample) to as large as a few degrees. From the behavior of the reflectivity one can infer properties of the sample such as material composition or thickness.

Figure 1:
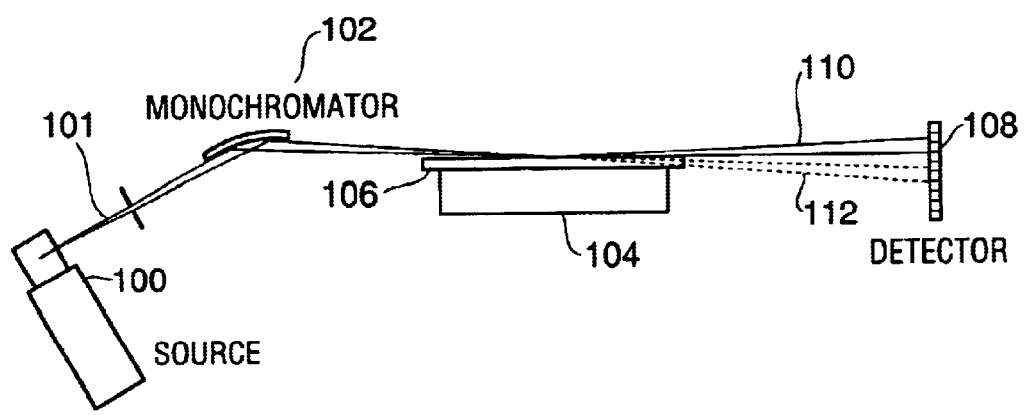
FIG. 1 is a simplified view of the of the measurement system disclosed in the '325 application.

A view of the XRR system disclosed in '325 application for simultaneous measurements of the reflectivity over a range of angles is shown in FIG. 1. As shown in FIG. 1 the source 100 generates an x-ray beam 101 that is incident upon an x-ray reflector 102, which is typically a monochromator. X-rays are then focused upon the sample being evaluated 106 which is positioned on a supporting stage 104. X-rays incident upon the sample are then reflected and detected with a position-sensitive detector 108 (such as a photodiode array).

Reflected x-rays 110 are captured in the top half of the detector 108, while the incident beam 112 can be measured by lowering the stage and reading the bottom half of the detector. By properly normalizing the two profiles (as described in the '325 application) one can determine the reflectivity as a function of angle. One of the key features of such a profile is the appearance of fringes whose spacing is inversely related to the thickness of the film under study.

Figure 2:
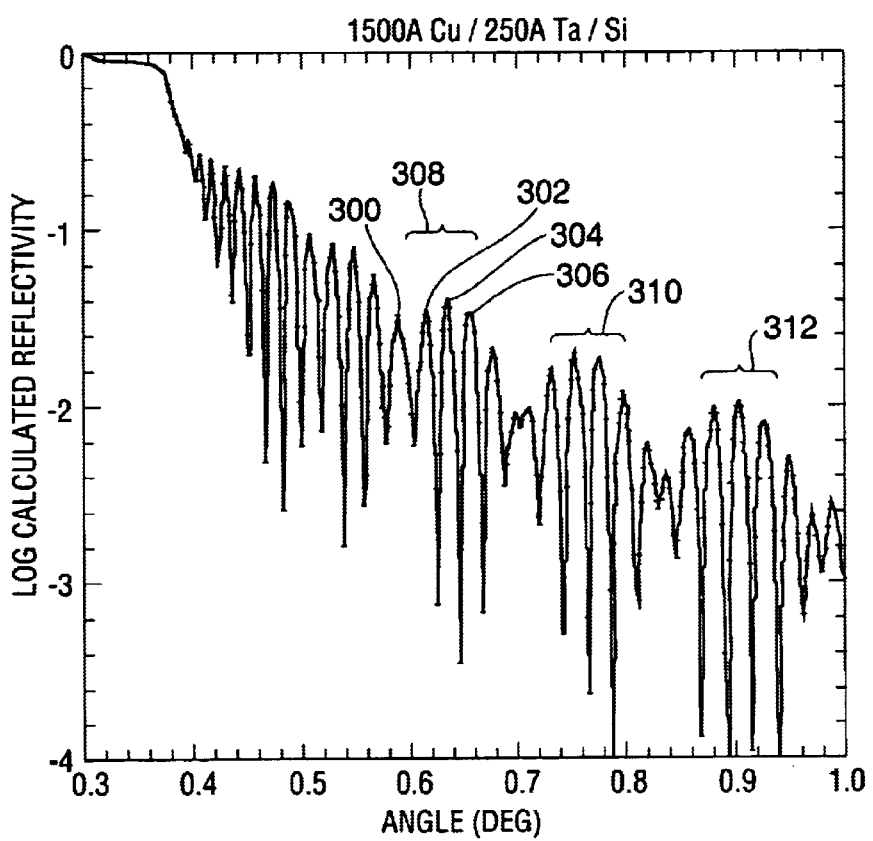
FIG. 2 is a graph showing the high-resolution fringe profile for a thin film sample.
Figure 3:
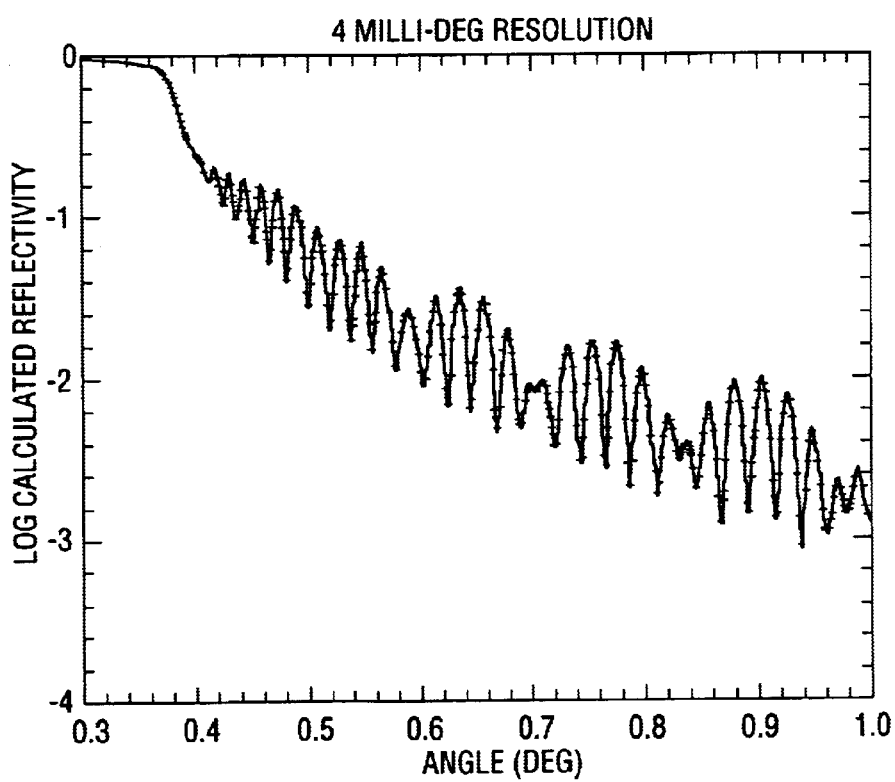
FIG. 3 is a graph showing the fringe profile for a thin film sample.
Figure 4:
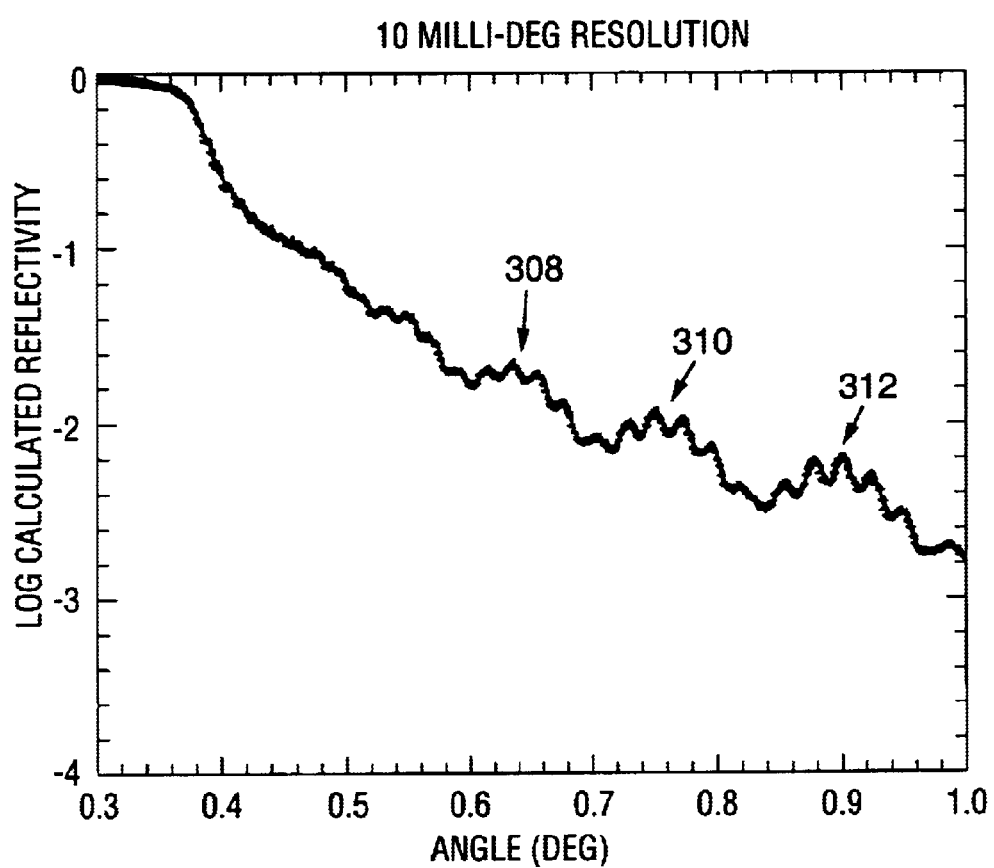
FIG. 4 is a graph showing a low-resolution fringe profile for a thin film sample.

FIG. 2 shows the reflectivity of a perfect, 1500 Å copper (Cu) film on top of 250 Å of tantalum (Ta) on top of a Si substrate. The fine fringes (e.g. 300, 302, 304, 306 in FIG. 2) arise from interference in the thick Cu layer; the broad envelope fringes (e.g. 308, 310, 312) arise from the interference in the thin Ta layer. The plot shown in FIG. 2, however, is idealized, and not what a real system would measure. In practice, the ability of the XRR system to resolve angle is limited. For instance, the finite-width of the individual detecting elements (pixels) of the photodetector leads to an averaging of a finite range of angles. In one embodiment a 2° angular range is covered by 500 pixels which means that the angular resolution is no better than 4 m° (i.e. 2 degrees divided by 500 pixels). The impact of this effect is illustrated in the graph of FIG. 3 which was generated assuming a 4 m° system resolution. Clearly the fringe contrast has been reduced as compared to FIG. 2. For a 10 m° system as shown in FIG. 4, the fringe contrast generated by the interference with the thick copper layer is attenuated to the point where, depending on the noise characteristics of the measurement, the fringes might not even be distinguishable. In contrast the fringes generated by the interference in the thinner layer of Ta are still visible (308, 310, 312).

Although the size of the detecting elements of the detector plays a role in the resolution of the system, it is not the only factor to consider. In real systems the x-ray source has a finite size which means the x-ray beam at focus (sample surface) will also have a finite size. This causes a smearing of angles which is illustrated in FIG. 5.

Figure 5:
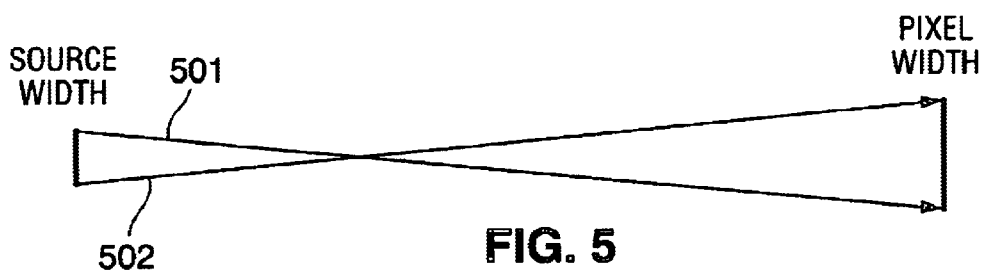
FIG. 5 illustrates the effect of pixel width and apparent x-ray source width on measurement resolution.

FIG. 5 shows the interplay between the source and a single pixel of the detector (the widths are grossly exaggerated for this illustration). The total angular range of data collected by this pixel is the difference between the angles of the two extreme rays 501, and 502 shown. As the source width is increased (i.e. the area of x-ray emission material is increased) the angular range collected by each pixel of the detector also increases. In fact, should the width of the source, at focus on the sample exceed that of the pixels it becomes the dominant effect in determining the system resolution. Alternatively, it can be appreciated that if the detector is moved farther away from the sample, the angular range would be reduced.

Figure 6A:
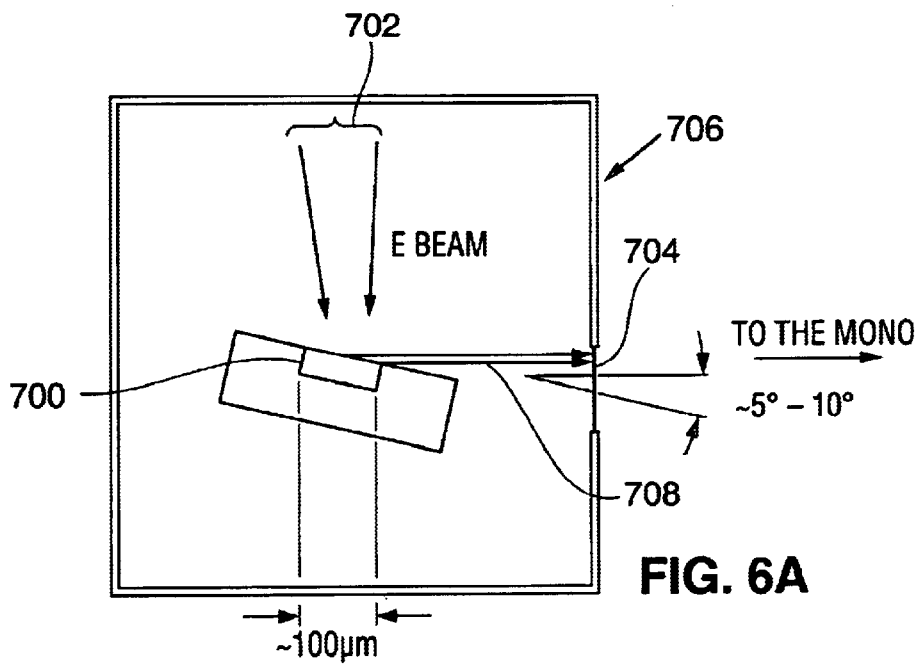
FIGS. 6(a-b) show an adjustable x-ray source where the take off angle of the x-ray emission material can be varied.
Figure 6B:
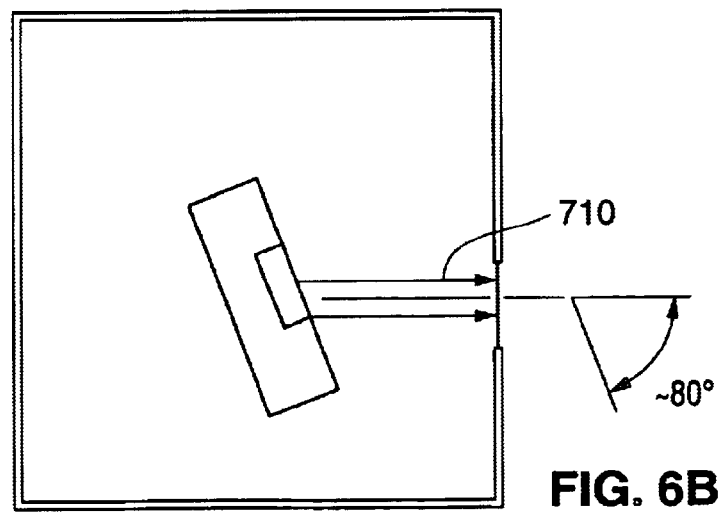

One way to improve the resolution is to use a smaller source. However, the size of the x-ray emission material 700, shown in FIGS. 6(a–b), is limited by the one's ability to focus the electron beam 702 (which is used to stimulate the x-ray emission material) and by thermal constraints (the smaller the x-ray emission material the harder it is to wick away the heat). In practice, the lower limit of length of the x-ray emission material 700 is in the range of 100 μm-500 μm. If an x-ray probe beam generated by the x-ray emission material were imaged onto the sample surface, with a width in this range, the degradation of the system resolution, due to the width of the probe beam, would far exceed that caused by the pixel width (which tends to be 25 μm in practice). (The actual size of the source imaged by the monochromator depends on the monochrometer acceptance angle and aberrations.) To minimize this degradation in resolution, the x-ray emission material 700 can be rotated relative to the optical system, such as monochromator, (which is used to focus the x-ray probe beam) so that the apparent width of source, as seen by the optical system, through an aperture 704 disposed in the housing 706 is reduced; thereby reducing the effective width of the x-ray probe beam. This is illustrated in FIGS. 6(a–b), where the effective width of the x-ray beam projected to the optical system, is related to the sine of the angle of the x-ray emission material 700 relative to the aperture 704 in the housing 706. The relationship is such that the effective x-ray probe beam 710 for an angle of approximately 80 degrees is significantly wider than the effective x-ray probe beam 708 for an angle of 5 degrees. Thus, by adjusting the angle of the x-ray emission material the effective width of the probe can be reduced to as little as approximately 5 μm. This angle of the x-ray emission material relative to the aperture is referred to as the take-off angle.

Figure 9:
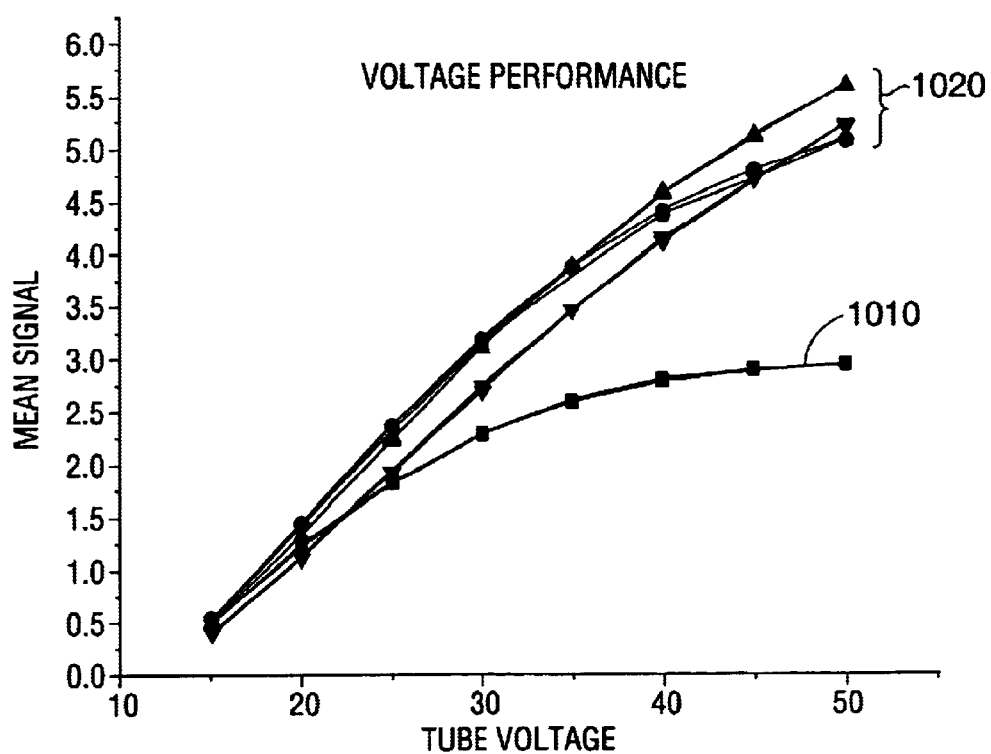
FIG. 9 shows the relationship between tube voltage and output flux as it relates to take off angle.

While reducing the take-off angle does limit the apparent source size, it comes at a price. One typically wants to run these tubes (i.e. the x-ray source) at high voltages to increase the x-ray flux of the line of interest (e.g., kα line). Theoretically, the boost in flux varies as the voltage to the 3/2 power. At higher voltages, however, the x-rays tend to get generated deeper in the target material. When this x-ray emission material is then tilted the x-rays have to tunnel through a substantial amount of material to make their way out of the x-ray source. This causes a substantial loss in flux. At some point, as the take-off angle is reduced, further increases in tube voltage return no increase in x-ray flux at all. This is illustrated in FIG. 9 where curve 1010 corresponds to the flux/voltage relationship for a very low take off angle, and curves 1020 correspond to the flux/voltage relationship at a higher take-off angles, such that an increase in voltage corresponds to an increase in flux over a wider range than for the low take take-off angle of 1010.

As is clear from the above there are a number of interrelated factors which lead to trade-offs in system performance. At small take-off angles a narrow x-ray probe beam is generated and potentially high resolution results; at large take-off angles a wider probe beam and a stronger signal results, but the resolution reduced.

Figure 7:
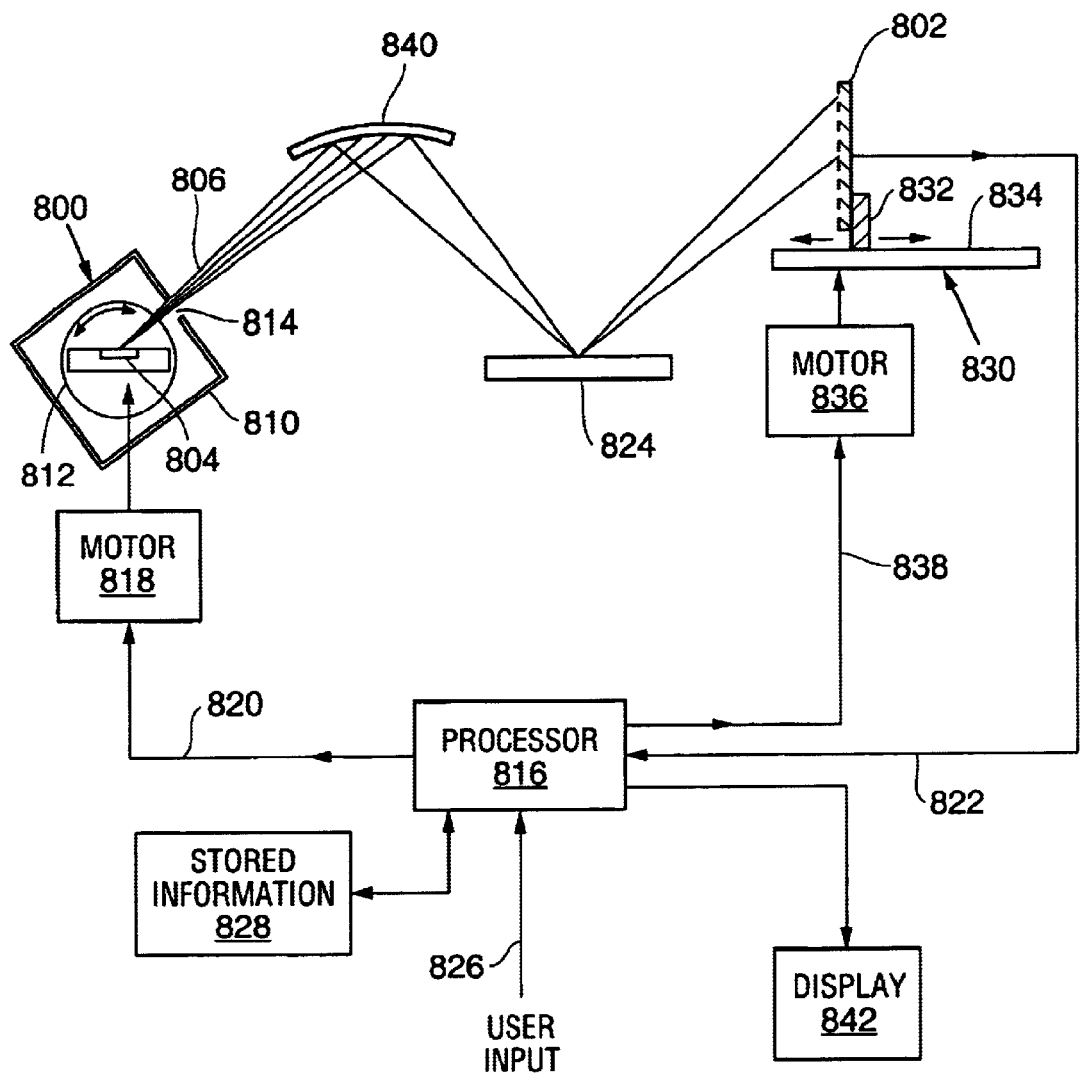
FIG. 7 shows an embodiment of an XRR measurement system with an adjustable x-ray source and an adjustable detector positioner.

FIG. 7 shows a system that provides an adjustable x-ray source 800 and an adjustable detector positioning device 830. As discussed above in connection with FIG. 6, an x-ray source 800 operates by projecting electrons into the x-ray emission material 804, which responds by projecting x-rays.

The x-ray emission material 804 is contained in a housing 810 and mounted to an adjustable mounting 812. In one embodiment the adjustable mounting 812 is rotatable, which allows for x-ray emission material 804 to be rotated relative to an the aperture 814 in the housing 810. This adjustable mounting 812 could be a rotating stage that is pivoted about an axis that runs horizontally through the x-ray emission material. The x-rays which are emitted through the aperture 814 form an x-ray probe beam that is reflected by the optical system 840, which focuses the x-ray probe beam on the sample 824. This optical system as discussed in the '548 patent can include a monochromator. As discussed above the effective width of the x-ray probe beam 806 is a function the take off angle of the x-ray emission material 804 relative to the aperture 814. In one embodiment the position of the adjustable mounting 812 can be controlled by a processor 816. The processor 816 sends signals 820 to a motor 818 which is coupled with the adjustable mounting 812 and causes it to rotate, and thereby change the take off angle of the x-ray emission material 804. In some circumstances it may be beneficial to provide a manual adjustor which is coupled to the adjustable mounting 812 so that an user can manually adjust the take off angle.

The processor 816 can include a number of separate processors and controllers or it could be a single processor. The term "processor" as used herein refers to processing elements used to process information and control elements of the measurement system. The processor 816 receives signals 822 from the detector 802, and based on the signals 822 determines the amplitude of x-rays relative to their angle of incidence on the sample 824. The processor can then uses this information to generate a display 842 of information, such as fringe information, as shown in FIGS. 2–4. Where the processor 816 determines that the features of the fringes are poorly defined due to poor resolution, as in FIG. 4, the processor can send a signal 820 to the motor 818 causing the rotation of the adjustable mounting 812 to reduce the take off angle. Alternatively, if the processor 816, detects that system is operating at a higher resolution than necessary, as in FIG. 2, then process can send a signal to the motor 818 causing motor to adjust the adjustable mounting 812 to increase the take off angle, thereby reducing the resolution, but increasing the speed of the measurement.

Alternatively, or in addition, the system can also allow the user to input information 826 regarding the thin film sample 824 to be measured. The processor can then access stored information 828 regarding the optimum settings for the adjustable x-ray source 800 for the particular characteristics of the sample 824 as input by the user, and adjust the position of the adjustable mounting 812 accordingly.

In a similar fashion the processor 816 can also control the positioning of the detector 802 relative to the sample that is being measured. In one embodiment the detector is mounted to a carriage 832 that is engaged with a positioning track 834, which allows the detector 802 to be moved either closer to, or further away from, the sample 824 being measured. It should be recognized that alternatively the system could allow for the sample, the x-ray source, and the optical system to move relative to the detector which could be fixed in single position. As shown in FIG. 7, the position of the detector 802 relative to the sample can be adjusted using a motor 836 that is controlled by signals 838 from the processor 816. For situations where it is difficult to resolve features of the fringe, as in FIG. 4, the processor 816 can send signals to the motor 836 causing the position the detector 802 to be move further from the sample 824, thereby increasing the resolution of the system. In other situations, where the resolution is greater than needed, the processor can send signals to the motor 836 causing the detector to be moved closer to the sample, which decreases the resolution but increases the speed with which measurements can be made. In some circumstances it may be beneficial to provide a manual adjustor which is coupled to adjustable detector positioning device to allow the user to manually adjust the position of the detector.

It should be recognized that while the system shown in FIG. 7 includes both a means for adjusting the apparent width of the source, and a means for adjusting the position of the detector, it may be preferable to implement a system which includes either the one or the other. As is apparent from the discussion above the resolution of the system can be adjusted by changing the position of the detector relative to the sample, or by changing the apparent width of the source. Thus, it is not necessary for a system to include the ability to adjust both the apparent width of the source and the position of the detector relative to the sample.

Figure 8:
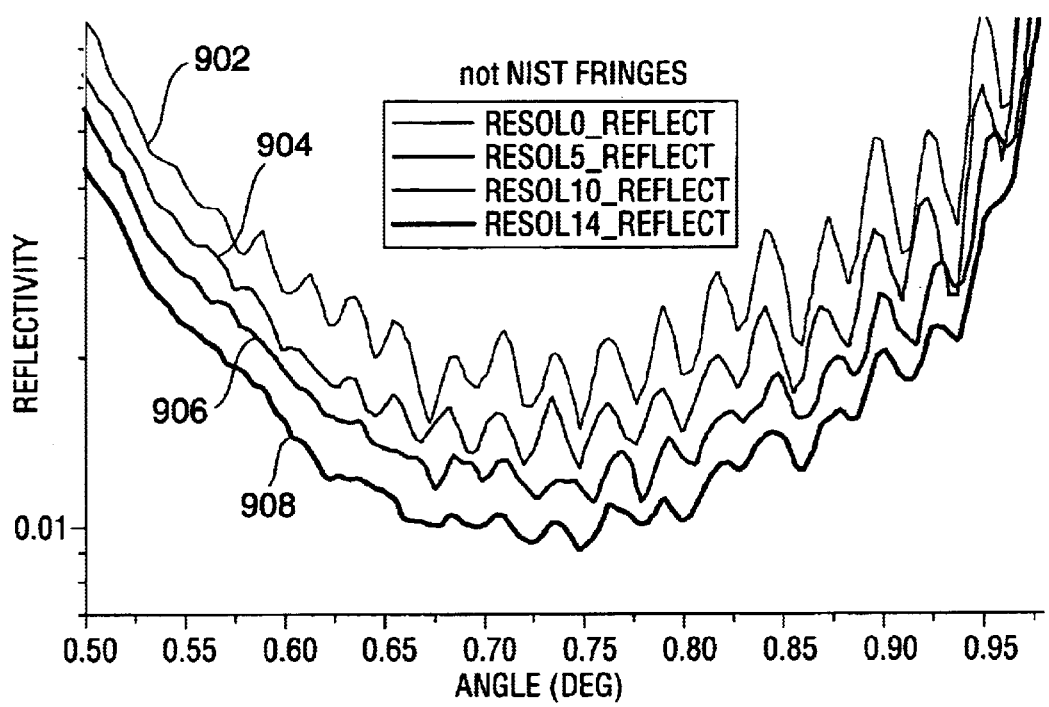
FIG. 8 shows the effect of varying take off angles on fringe resolution for a thin film sample.

FIG. 8 shows the resolution and output powers for several different take-off angles. In FIG. 8 the four curves 902, 904, 906 and 908 have been spatially separated for clarity. The top curve 902 represents the smallest take-off angle; five degrees. The three curves 904, 906 and 908 below the top curve represent take-off angles of ten, fifteen and nineteen degrees respectively. As can be seen, as the take-off angle is reduced (so that the effective width of the x-ray probe beam is reduced), the peaks become more pronounced and can be more easily analyzed.

While the method and apparatus of the present invention has been described in terms of its presently preferred and alternate embodiments, those skilled in the art will recognize that the present invention may be practiced with modification and alteration within the spirit and scope of the appended claims. The specifications and drawings are, accordingly, to be regarded in an illustrative rather than a restrictive sense. Further, even though only certain embodiments have been described in detail, those having ordinary skill in the art will certainly understand that many modifications are possible without departing from the teachings thereof. All such modifications are intended to be encompassed within the following claims.

What is claimed is:

1. An adjustable measurement system for evaluating characteristics of a sample using an x-ray probe beam, comprising:

an adjustable x-ray source that generates the x-ray probe beam, where an effective width of the x-ray probe beam can be modified by tilting the adjustable x-ray source with respect to the sample being evaluated;

an optical system for focusing the x-ray probe beam onto the surface of the sample, such that the x-ray probe beam is reflected off the sample;

a detector that receives the x-ray probe beam reflected off the sample, and generates a plurality of signals in response to receiving the x-ray probe beam; and a processor for analyzing the plurality of signals generated by the detector to evaluate characteristics of the sample.

2. The adjustable measurement system of claim 1 wherein the adjustable x-ray source comprises:

an x-ray emission material that generates x-rays;

a housing that contains the material, where the housing has an aperture through which the x-ray probe beam is projected toward the optical system;

an adjustable mounting for holding the x-ray emission material, such that the position of the x-ray emission material can be adjusted relative to the aperture.

3. The adjustable measurement system of claim 2 further comprising a first motor coupled to the adjustable mounting, and controllable by the processor such that the processor can adjust the position of the x-ray emission material relative to aperture.

4. The adjustable measurement system of claim 3 further comprising:

a detector position adjustor for adjusting the position of the detector relative to the sample, wherein the detector is mounted to detector position adjustor so that the position of the detector can be adjusted.

5. The adjustable measurement system of claim 4 wherein the detector position adjustor comprises a track, and a carriage which is engaged with the track, such that the carriage can be moved to a plurality of positions relative to the track, and wherein the detector is mounted to the carriage.

6. The adjustable measurement system of claim 4 further comprising a second motor coupled to the detector position adjustor and controllable by the processor such that the processor can adjust the position of the detector by sending a signal to the second motor.

7. The adjustable measurement system of claim 6 wherein the processor analyzes characteristics of the x-ray probe beam received by the detector, and based on the analysis sends a signal to the second motor to which causes the second motor to adjust the position of the detector.

8. The adjustable measurement system of claim 6 further comprising:

an user input device, coupled to the processor, which allows the operator to input information regarding the sample to be measured;

wherein the processor operates to analyzes the information regarding the sample, and based on this information adjusts the position of the detector.

9. The adjustable measurement system of claim 3 wherein the processor analyzes characteristics of the x-ray probe beam received by the detector, and based on the analysis generates a signal that causes the first motor to adjust the position of the x-ray emission material relative to the aperture.

10. The adjustable measurement system of claim 3 further comprising:

an user input device coupled to the processor, which allows the user to input information to the processor regarding the sample to be measured; and wherein the processor operates to analyze user input information regarding the sample, and based on this information adjusts the position of the adjustable mounting.

11. The adjustable measurement system of claim 1 further comprising a means for adjusting a take-off angle of an x-ray emission material contained in the adjustable x-ray source, thereby adjusting the resolution of the system.

12. The adjustable measurement system of claim 1, further comprising a manual adjustor coupled to the adjustable x-ray source such that an user can manually adjust a characteristic of the x-ray probe beam.

13. The adjustable measurement system of claim 1 further comprising:

a detector position adjustor, wherein the detector is coupled to the detector position adjustor such that the detector can be moved relative to the sample; and a manual adjustor coupled to the detector position adjustor such that a user can manually adjust the detector position adjustor.

14. An adjustable measurement system for evaluating characteristics of a sample using an x-ray probe beam, comprising:

an x-ray source that generates the x-ray probe beam, the x-ray source having an adjustable tilt with respect to the sample being evaluated, the determining the effective width of the x-ray probe beam;

an optical system for focusing the x-ray probe beam onto the surface of the sample, such that the x-ray probe beam is reflected off the sample;

a detector which receives the x-ray probe beam reflected off the sample, and generates a plurality of signals in response to receiving the x-ray probe beam;

a detector position adjustor wherein the detector is mounted to the detector position adjustor, and the detector position adjustor can move the detector to a plurality of positions relative to the sample being detected, where the position is determined by characteristics of the sample being evaluated; and a processor for analyzing the plurality of signals generated by the detector to evaluate characteristics of the sample.

15. The adjustable measurement system of claim 14 wherein the detector position adjustor includes a track and a carriage engaged with the track such that the carriage can move along the track, and wherein the detector is mounted to the carriage.

16. The adjustable measurement system of claim 15 further comprising a motor coupled to the detector position adjustor which is controllable by the processor such that the processor can adjust the position of the detector relative to the sample by sending a signal to the motor.

17. The adjustable measurement system of claim 16 wherein the processor analyzes the x-ray probe beam received by the detector, and based on the analysis generates a signal that causes the motor to adjust the position of the detector.

18. The adjustable measurement system of claim 16 further comprising:

an user input device, which allows the operator to input information regarding the sample to be measured;

wherein the processor operates to analyze the information regarding the sample and based on this sends a signal to the motor.

19. The adjustable measurement system of claim 14 further comprising a manual adjustor coupled to the detector position adjustor such that a user can manually adjust the position of the detector, based on the sample being measured.

20. A method for making adjustments to a measurement system for evaluating a plurality of different samples, the method comprising:

generating an x-ray probe beam using an x-ray source, which includes an x-ray emission material;

focusing the x-ray probe beam onto an one of the plurality of different samples;

detecting the x-ray probe beam after the beam has been reflected off the one of the plurality of different samples;

generating a plurality of signals corresponding to the detected x-ray probe beam;

analyzing the plurality of signals to evaluate the one of the plurality of different samples; and adjusting the resolution of the system based on the analysis of the plurality of signals by tilting the x-ray source with respect to the one of the plurality of different samples in order to change an effective width of the x-ray beam.

21. The method of claim 20 further wherein the adjusting of the resolution of the system comprises adjusting a take off angle of the x-ray emission material.

22. A method for making adjustments to a measurement system for evaluating a sample, the method comprising:

generating an x-ray probe beam using an x-ray source which includes an x-ray emission material;

focusing the x-ray probe beam onto the sample;

detecting the x-ray probe beam after the beam has been reflected off the sample;

generating a plurality of signals corresponding to the detected x-ray probe beam;

analyzing the plurality of signals to evaluate the sample;

receiving user input information regarding the sample to be measured; and based on the user information adjusting the resolution of the system by tilting the x-ray source with respect to the sample in order to change an effective width of the x-ray probe beam.

23. The method of claim 22 further wherein the adjusting of the resolution comprises adjusting a take off angle of the x-ray emission material.

24. A method for making adjustments to a measurement system for evaluating a sample, whereby adjustments change a resolution of the system, the method comprising:

generating an x-ray probe beam;

modifying an effective width of the x-ray beam by tilting a source generating the x-ray probe beam;

focusing the x-ray probe beam onto the sample;

detecting the x-ray probe beam after the beam has been reflected off the sample;

generating a plurality of signals corresponding to the detected x-ray probe beam;

analyzing the plurality of signals to evaluate the sample; and in response to the analysis, moving the detector relative to the sample to change the resolution of the system.

25. A method for making adjustments to a measurement system for evaluating a sample, whereby adjustments change a resolution of the system, the method comprising:

generating an x-ray probe beam;

modifying an effective width of the x-ray beam by tilting a source generating the x-ray probe beam;

focusing the x-ray probe beam onto the sample;

detecting the x-ray probe beam after it has been reflected off the sample;

generating a plurality of signals corresponding to the detected x-ray probe beam;

receiving user input information regarding the sample to be evaluated; and in response to the user input information regarding the sample, moving the detector relative to the sample to change the resolution of the system.

26. An adjustable measurement system for evaluating characteristics of a sample using an x-ray probe beam, comprising:

an x-ray source, which includes an x-ray emission material, that generates the x-ray probe beam;

an optical system for focusing the x-ray probe beam onto the surface of the sample, such that the x-ray probe beam is reflected off the sample;

a detector that receives the x-ray probe beam reflected off the sample, and generates a plurality of signals in response to receiving the x-ray probe beam;

a processor for analyzing the plurality of signals generated by the detector to evaluate characteristics of the sample; and a means for adjusting a tilt of the x-ray source in order to adjust the resolution of the system to account for characteristics of the sample by adjusting an effective width of the x-ray probe beam.

27. The measurement system of claims 26 wherein the means for adjusting the tilt includes a rotatable mounting so that a take-off angle of the x-ray emission material can be adjusted.

28. The measurement system of claim 26 further comprising means for adjusting the resolution of the system by adjusting the position of the detector relative to the sample.

29. The measurement system of claim 26 wherein the means for adjusting the tilt includes a means for adjusting a take off angle of the x-ray emission material, and further comprising means for adjusting the position of the detector relative to the sample.

30. An apparatus for evaluating a sample comprising:

a source of x-rays;

an optical system for focusing the x-rays onto the surface of the sample such that the x-rays create a range of angles of incidence with respect to said surface;

a detector having an array of individual detecting elements oriented to receive x-rays reflected from the sample having a range of angles of incidence with respect to the sample wherein each element receives a portion of the reflected x-rays with the angle of incidence of the rays striking any given individual detecting element being a function of a position of the individual detecting element within the array; and a mechanism for adjusting an angular spread of the x-rays striking the individual detecting elements in the array by tilting the source of x-rays, so that a resolution of the apparatus can be adjusted to optimize the evaluation of the sample.

31. The apparatus of claim 30 wherein the mechanism further controllably varies the position of the detector relative to the sample.

32. An apparatus are recited in claim 30 wherein the mechanism controllably adjusts a take-off angle of the x-ray source.

33. An apparatus as recited in claim 30 wherein the mechanism controllably adjusts an apparent width of the x-ray source as imaged on the sample.

* * * * *